United States Patent [19]

Zirino

[11] Patent Number: 5,419,826
[45] Date of Patent: May 30, 1995

[54] ION-SELECTIVE REFERENCE PROBE

[75] Inventor: Albert R. Zirino, San Diego, Calif.

[73] Assignee: The United States of America as represented by the Secretary of the Navy, Washington, D.C.

[21] Appl. No.: 219,680

[22] Filed: Mar. 25, 1994

[51] Int. Cl.$^6$ .............................................. G01N 27/26
[52] U.S. Cl. .................................... 204/416; 204/433; 204/435; 204/414; 204/420; 204/413; 422/82.03
[58] Field of Search ............... 204/433, 435, 416, 418, 204/419, 413, 414, 420; 422/82.03

[56] References Cited

U.S. PATENT DOCUMENTS

| | | | |
|---|---|---|---|
| 3,705,089 | 12/1972 | Grubb | 204/435 |
| 4,002,547 | 1/1977 | Neti et al. | 204/435 |
| 4,282,079 | 8/1981 | Chang et al. | 204/420 |
| 4,312,734 | 1/1982 | Nichols | 204/420 |
| 4,390,406 | 6/1983 | Kato et al. | 204/435 |
| 4,495,050 | 1/1985 | Ross, Jr. | 204/435 |
| 4,602,987 | 7/1986 | Bonaventura et al. | 204/129 |
| 4,629,544 | 12/1986 | Bonaventura et al. | 204/129 |
| 4,644,285 | 2/1987 | Britton | 204/400 |
| 4,761,209 | 8/1988 | Bonaventura et al. | 204/129 |
| 4,851,104 | 7/1989 | Connery et al. | 204/416 |
| 4,952,289 | 8/1990 | Ciccone et al. | 204/129 |
| 4,959,135 | 9/1990 | Zenner et al. | 204/129 |
| 4,959,138 | 9/1990 | Brinkmann et al. | 204/435 |
| 5,034,113 | 7/1991 | Iwamoto | 204/435 |
| 5,071,526 | 12/1991 | Pletcher et al. | 204/400 |
| 5,071,537 | 12/1991 | Yamaguchi et al. | 204/435 |

*Primary Examiner*—Kathryn Gorgos
*Assistant Examiner*—Bruce F. Bell
*Attorney, Agent, or Firm*—Harvey Fendelman; Thomas Glenn Keough

[57] ABSTRACT

An ion-selective reference probe which is adapted for use with potentiometric measurement systems is disclosed. The reference probe is non-chloride based and employs a specially adapted electrolyte which is reversible (i.e. with regard to ionic activity). More particularly, the electrolyte includes appropriate concentrations of ethylenediamine and copper(II) ions in a solvent to permit reversibility of the electrolyte within a desired range. Junction potential between the electrolyte and a test solution is minimized by forming the electrolyte from a portion of the test solution.

22 Claims, 1 Drawing Sheet

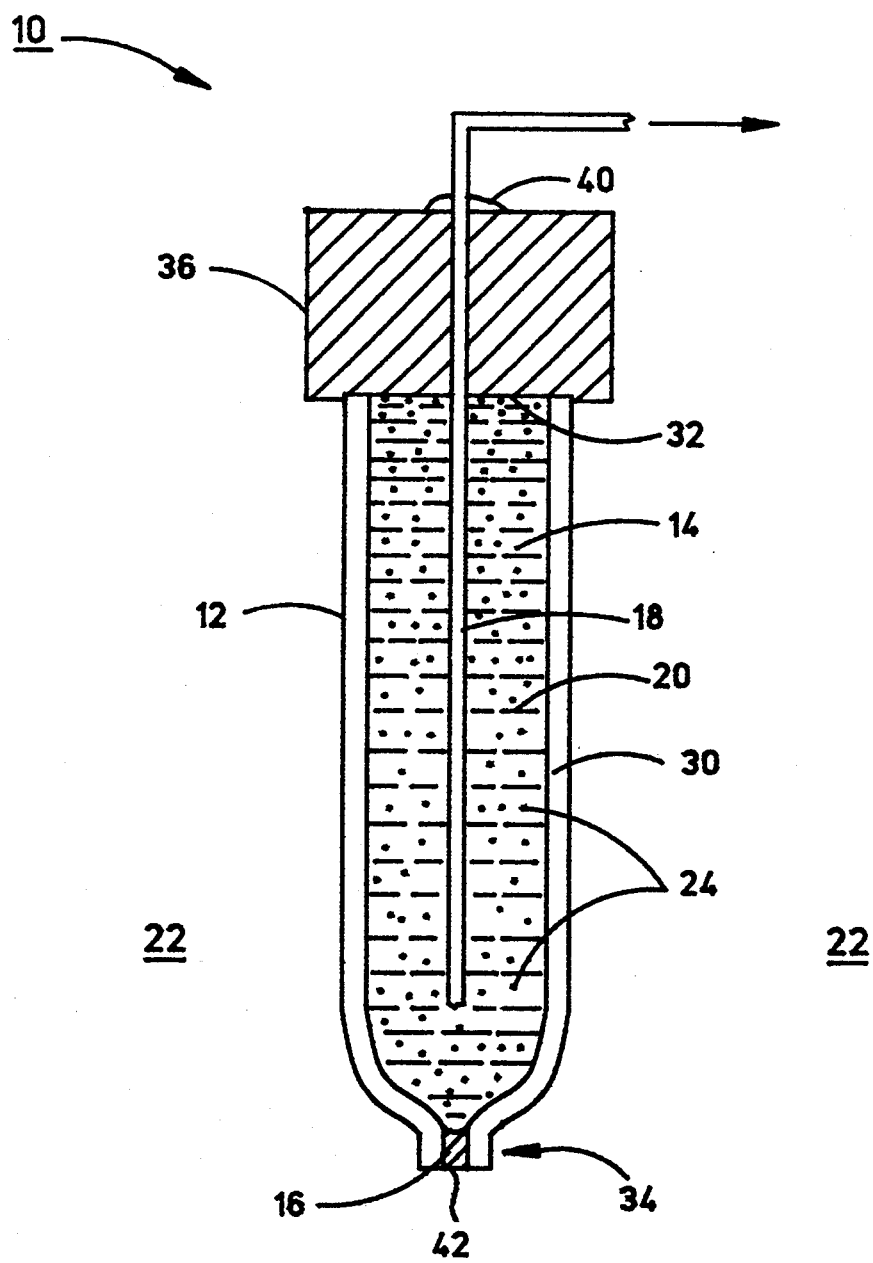

ION-SELECTIVE REFERENCE PROBE

This invention described herein may be manufactured and used by or for the Government of the United States of America for governmental purposes without the payment of any royalties thereon or therefor.

BACKGROUND OF THE INVENTION

This invention broadly relates to ion-selective electrodes, and more particularly to reference probes for potentiometric measurement of ion-concentrations in a test solution.

Metals have long been known to contaminate aquatic environments. Copper, for example, often leeches from marine paints into harbors and causes aquatic contamination. Copper ion concentration profiles are useful to precisely determine the extent of copper contamination. With contamination levels known, effective remedial measures can be chosen. Accordingly, deep water devices have been developed which profile contaminate concentrations in sea water. Such devices may rely on potentiometric measurement techniques.

Simple potentiometric measurement systems typically employ an electrode pair immersed in a test solution. The pair includes a reference electrode and a working electrode. In operation, a minute current (e.g. $10^{-9}$ amps) is drawn between the electrode pair for an instant (e.g. 1 second) to make a voltage reading. The amount of charge drawn is so small that ion concentrations in the test solution are not significantly affected. The measured voltage potential between the electrode pair indicates ion concentrations. Importantly, the reference electrode maintains a stable potential to enable meaningful measurements by the working electrode.

A typical reference electrode includes a housing for holding a reference element in an electrolyte. This arrangement forms a half-cell which provides the reference potential needed for meaningful potentiometric measurements. Ionic communication is permitted between the electrolyte and the test solution through a junction in the housing.

The most common types of ion-selective reference electrodes utilize a reference element made from silver-silver chloride (Ag/AgCl) or mercury-mercurous chloride and a chloride-based electrolyte such as a saturated aqueous solution of potassium chloride. One such reference electrode is disclosed in U.S. Pat. No. 3,705,089 by Grubb. Such electrodes form measurable amounts of solids (e.g. silver chloride) during operation from ions dissolved in the aqueous solution. Reactions involving solid formations, however, are notoriously slow and chemically irreversible. Additionally, electron drift and hysteresis resulting from pressure and temperature changes reduces measurement accuracy. A significant junction potential between the electrolyte and test solution further limits measurement accuracy.

Noteworthy attempts to increase measurement accuracy by reducing hysteresis due to temperature and pressure changes manifest themselves in U.S. Pat. No. 4,495,050 by Ross and U.S. Pat. No. 4,959,138 by Brinkmann et al., respectively. Both inventions, however, rely on a chloride based electrolyte. Ionic measurements taken with these devices rely on solid formation. As a consequence, ionic reactions are irreversible and ionic measurements are not optimally accurate.

The present inventive concept overcomes the above limitations by providing a reference electrode probe which employs a specially adapted electrolyte. The electrolyte does not depend on solid formation. Instead, ionic activity in the electrolyte is freely reversible. The electrolyte also includes a solvent formed from a portion of the test solution to minimize associated junction potential and increase measurement accuracy. With these modifications, the present invention is particularly suitable for use with accurate potentiometric profiling of ion concentrations in the ocean.

SUMMARY AND OBJECTS OF THE INVENTION

The present inventive concept provides a non-chloride based reference probe. The reference probe is ion-selective and adapted for use with potentiometric measurement systems. The reference probe employs a specially adapted electrolyte which is reversible (i.e. with regard to ionic activity). In the preferred embodiment, ethylenediamine and copper(II) ions complex in appropriate concentrations to permit reversibility of the electrolyte. The electrolyte may include an appropriate buffer to stabilize changes in pH over a desired range of pressure and temperature. The electrolyte includes a solvent formed with a portion of the test solution to reduce associated junction potential.

Since operation of this reference probe does not rely on formation of solids, but instead on a reversible ionic movement, a constant potential is more accurately maintained which enables accurate periodic measurements. Additionally, since the electrolyte is characterized by reversibility, changes in temperature and pressure associated with deep water profiling will not adversely affect the reference potential for subsequent measurements.

Accordingly, an object of the present invention is to provide an ion-selective probe capable of making potentiometric measurements of copper(II) ion concentrations in a test solution.

Another object of the present invention is to provide a non-chloride reference probe for use with a working electrode to facilitate repeatable potential measurements to within 0.6 mV and accurate potential measurements over a range of greater than 6 mV.

Yet another object of the present invention is to provide an ion selective probe that measures copper(II) ion activity in a test solution without stripping away ions from the test solution so that measurements are accurately reproducible.

Still another object of the present invention is to provide an probe which is corrosion resistant for enhanced life in a marine environment.

A further object of the invention is to prepare a seawater reference probe which is reversible to temperature and pressure changes similar to gradients encountered in oceanic profiles.

Another object of the present invention is to prepare a reference probe in-situ with a solvent formed from the test solution to minimize junction potential with the test solution.

Yet another object of the invention is to provide a chloride independent electrode which does not rely on solid formation and is simple and cost effective to use.

These and other objects, advantages and novel features of the invention will become apparent from the following description of the preferred embodiment of the invention when considered in conjunction with the accompanying drawing.

BRIEF DESCRIPTION OF THE DRAWING

The drawing is a cross-sectional view of the reference probe of the present invention.

DESCRIPTION OF THE PREFERRED EMBODIMENT

Referring to the drawing an ion-selective reference probe 10 for potentiometric determination of ion concentrations in a test solution is shown. Probe 10 includes a housing 12 formed with a hollow interior 14 for containing electrolyte 20. A reference element 18 is held within housing 12 and is surrounded by electrolyte 20 which is specifically designed to be reversible over a desired range of temperatures and pressures. More particularly, electrolyte 20 is formed from a reversible metal-ligand complex to permit reversible ionic reactions with reference element 18.

In the preferred embodiment of electrolyte 20, copper(II) ions 24 function as the primary carrier of ionic current. A pH buffer stabilizes the pH of electrolyte 20. A reversible complexing agent such as ethylenediamine or glycine buffers the rate of ionic activity in electrolyte 20 against small changes in copper(II) ion concentration. Copper(II) ionic activity in electrolyte 20 is, thus, reversible to changes in pressure and temperature associated with use through various oceanic depths. Additionally, measurement delay which normally accompany temperature and pressure changes are inhibited by rapid reversibility of copper(II) ionic activity. In successful tests, the electrolyte includes a copper(II) ion concentration of $4 \times 10^{-4}$ M and an ethylenediamine concentration of $2 \times 10^{-3}$ M.

Although a copper(II) ions and ethylenediamine are employed in the preferred embodiment, it can be appreciated that any reversible electrolyte may be employed. It is known that various other reversible metal-ligand complexing agents having suitable concentrations of metal ions may be adapted for use as a reversible electrolyte for a potentiometric measurement probe in accordance with the present inventive concept.

Electrolyte 20 is formed from a viscous and incompressible solvent to assure proper ionic response at deep sea pressures and temperatures. The solvent is formed from a portion of test solution 22 to have a composition corresponding to the composition of test solution 22 to minimize junction potential between electrolyte 20 and test solution 22. In the preferred embodiment, test solution 22 is sea water. Electrolyte 20, therefore includes sea water as a solvent. It can be appreciated, however, by those skilled in the art that any suitable solvent having minimal junction potential with the test solution may be used which does not interfere with ionic measurement. For example a test solution of fresh water (as found in lakes and rivers) will require an electrolyte which exhibits minimal junction potential with the fresh water. Accordingly, fresh water may be used as the solvent. To avoid possible organic contamination of the electrolyte, in-situ fabrication of the reference probe is desirable just prior to use.

Reference element 18 is surrounded by electrolyte 20 within housing 12 and is electrically connected with a voltage measurement device of a potentiometric measurement system. Reference element 18, more particularly, is fabricated from electrically conductive material having an appropriate ionic composition to permit ionic communication with said electrolyte while maintaining a constant potential. In the preferred embodiment, reference element is a 14 k gold wire having sufficient copper to maintain a constant potential by permitting copper(II) ionic communication with electrolyte 20 and sufficient gold to resist forming solids, resist corrosion, resist oxidation and endure harsh marine environments.

In an alternate embodiment, reference element 18 is a copper(II) ion-selective electrode such as one which employs a copper crystal membrane. Reference element can be a commercially available electrode such as an Orion 94-29 ion-selective electrode manufactured by Orion Corporation.

Referring again to the drawing, housing 12 of reference probe 10 is shown and is made of electrically insulating material and is formed with an aperture 16. More particularly, housing 12 is a glass tube 30 formed having a first open end 32 and a second open end 34. Aperture 16 is defined by second open end 34 to permit ionic communication between electrolyte 20 and test solution 22. A cap 36 covers first open end 32 of housing 12. Reference element 18 extends through cap 36 and into hollow interior 14 where electrolyte 20 is enclosed. Silicone cement 40 forms a water-tight seal between reference element 18 and cap 36. An ion-permeable plug 42, held within aperture 16 permits ionic communication between electrolyte 20 and test solution 22 and prevents outflow of electrolyte 20 into test solution 22. Ion-permeable plug 42 may be fabricated from any material well-known in the art such as cotton fiber.

Although housing 12 is a tube as shown in the drawing, housing 12 may be of any geometric configuration, or, any suitable configuration commonly employed by those skilled in the art of potentiometry. More particularly, housing 12 is configured having a geometry suitable for resisting underwater pressure. Additionally, the junction formed at aperture 16 may be adapted to permit ionic communication in any way, well-known in the art. For example, a membrane, having a minimal junction potential may be used.

IN OPERATION

Electrolyte is fabricated by in-situ sampling of a portion of test solution 22 for use as a solvent. The solvent is mixed with an appropriate complexing agent. The pH is measured and an appropriate pH buffer may be added to stabilize electrolyte pH as necessary. Selected metal ions are added. The concentration of metal ions and complexing agent are appropriately adjusted and the pH is stabilized to buffer metal ion activity with respect to small changes in metal and ligand concentration. Accordingly, a reversible electrolyte is formed. In the preferred embodiment, the solvent is sea water, ethylenediamine is the metal complexing agent and copper(II) ions are complexed to form electrolyte 20. Electrolyte 20 is gelled by addition of (5%) agar gel in a concentration of five grams/liter. The resulting mixture is heated and permitted to cool in the housing. The gel functions to support the housing and cooperates with the housing to resist high operational pressure such as found in deep ocean water. Additionally, the gel prevents outflow of electrolyte 20 into test solution 22 to prevent contamination of test solution 22.

Reference element 18 is inserted and through first open end 32 of housing 12 and into electrolyte 20. With reference element 18 in place, ionic communication between the reference element 18 and test solution 22 is permitted via electrolyte 20. Reference probe 10 is appropriately connected to and employed with a potentiometric measurement system having at least one working electrode. More particularly, reference element 18 electronically connects with an appropriate voltage sensor such as a voltage follower or potentiometer. A stable potential is generated and potentiometric measurements are made. The potentiometric system may be used in conjunction with various measurement devices such as pH sensors, salinity sensors and thermometers, for example.

As disclosed, the present inventive concept is particularly useful with potentiometric measurement of metal ion concentrations. While the inventive concept is described in terms of a preferred embodiment, it can be appreciated by those skilled in the art, that certain changes and modifications can be made without departing from the scope of the invention. Substitution of another electrolyte is likely to accommodate applications other than oceanic profiling, for example. The scope of the appended claims are, therefore, to be understood as including each likely change or modification.

I claim:

1. A non-solid-forming reference probe for potentiometric determination of ion concentrations in a test solution comprising:
   a housing of electrically insulating material, said housing having a hollow interior and an aperture;
   a non-solid-forming sensing element held within said housing in said hollow interior; and
   an electrolyte enclosed within said housing surrounding said non-solid-forming sensing element and establishing ionic communication with the test solution through said aperture, said electrolyte having a reversible metal-ligand complex permitting reversibility of ionic communication between said electrolyte and said non-solid-forming sensing element.

2. A probe as recited in claim 1 wherein the test solution is sea-water and wherein said electrolyte is formed with a seawater solvent to minimize junction potential between said electrolyte and the test solution.

3. A probe as recited in claim 1 wherein said reversible metal-ligand complex includes a complexing agent and complexed metal ions in concentrations permitting reversibility of said electrolyte, said complexing agent is chosen from the group consisting of glycine and ethylenediamine.

4. A probe as recited in claim 3 wherein said non-solid-forming sensing element is a metal wire fabricated from a metal having ions characteristic of said complexed metal ions in said electrolyte permitting ionic communication between said non-solid-forming sensing element and said electrolyte.

5. A probe as recited in claim 4 wherein said electrolyte is formed with a copper(II) ions in a concentration of $4 \times 10^{-4}$ M and ethylenediamine in a concentration of $2 \times 10^{-3}$ M.

6. A probe as recited in claim 5 wherein said non-solid-forming sensing element is a 14 k gold having a copper content that maintains an ionic potential and a gold content that is non-corrosive.

7. A probe as recited in claim 4 wherein said non-solid-forming sensing element is a copper (II) ion-selective electrode.

8. A probe as recited in claim 3 wherein said housing is a glass tube and an ion-permeable plug is fastened within said aperture maintaining said electrolyte within said housing and preventing ionic contamination of the test solution.

9. A probe as recited in claim 8, wherein said glass tube includes first open end having a cap and a second open end, said non-solid-forming sensing element extends through said cap, said cap is formed with silicone cement sealing said non-solid-forming sensing element with said cap and said aperture is formed at a second open end of said glass tube permitting said ionic communication between said electrolyte and the test solution.

10. A non-solid-forming reference probe for potentiometric determination of ion concentrations in test solution comprising:
    a glass tube formed with a first open end and a second open end, said second open end defining an aperture;
    a reversible electrolyte enclosed within said glass tube, said electrolyte including ethylenediamine and metal ions permitting ionic reversibility of said electrolyte through a range of temperature, pressure and pH and said electrolyte including a solvent formed from a portion of said test solution minimizing junction potential between said electrolyte and said test solution; and
    a non-solid-forming sensing element extending through said first open end and into said electrolyte permitting said ionic reversibility without the formation of solids.

11. A probe as recited in claim 10 wherein said electrolyte includes copper (II) ions functioning as the primary carrier of ionic charge and wherein said non-solid-forming sensing element is a 14 k gold wire having copper providing a stable ionic potential and gold inhibiting solid formation with said electrolyte.

12. A probe as recited in claim 11 wherein said non-solid-forming sensing element is held by a cap which covers said first open end and wherein silicone cement seals said reference element with said cap.

13. A probe as recited in claim 12 further comprising:
    an ion-permeable plug held within said aperture permitting ionic communication between said electrolyte and said test solution and preventing contamination of said test solution by said metal-ligand complex.

14. A probe as recited in claim 13 wherein said electrolyte includes a $2 \times 10^{-3}$ M concentration of ethylenediamine and a $4 \times 10^{-4}$ M concentration of copper(II) ions.

15. A probe as recited in claim 10 wherein said non-solid-forming sensing element is a copper ion-selective electrode.

16. A in-situ method of providing reversible repeated potentiometric measurements of a test solution comprising:
    sampling the test solution;
    combining ethylenediamine with said sampled test solution;
    adding a metal ion to said ethylenediamine solution forming a reversible electrolyte;
    gelling said electrolyte in an electrically insulating housing, said housing having a first open end, a hollow interior for holding said electrolyte and a second open end having an aperture; and
    inserting a non-solid-forming sensing element through said first open end into said electrolyte permitting ionic communication without the formation of solids between said non-solid-forming sensing element and the test solution through said electrolyte and said aperture, said inserting being repeated allowing said reversible electrolyte to effect reversible ionic reactions with said non-solid-forming sensing element.

17. A method as recited in claim 16 wherein said electrolyte contains copper(II) ions for carrying ionic charge and said non-solid-forming sensing element is fabricated from copper for providing a constant ionic potential.

18. A method as recited in claim 17 wherein said non-solid-forming sensing element is a 14 k gold wire to resist corrosion.

19. A method as recited in claim 17 wherein said non-solid-forming sensing element is a copper ion-selective electrode having a copper crystal membrane.

20. A method as recited in claim 16 wherein said electrolyte maintains a stable pH and includes a concentration of copper(II) ions on the order of $10^{-4}$ M, and a concentration of ethylenediamine on the order of $10^{-3}$ M to buffer copper(II) ion activity against small changes in copper(II) ion concentrations.

21. A method as recited in claim 16 wherein said step of gelling said electrolyte includes:
   adding (5%) agar gel in a concentration of five grams/liter to said electrolyte; heating the agar gel/electrolyte mixture; and allowing a cooling of the agar gel/electrolyte mixture in said housing.

22. A method as recited in claim 16 further comprising:
   employing said non-solid-forming reference probe in said test solution establishing ionic communication between said non-solid-forming sensing element and said test solution through said electrolyte and a determining of copper (II) ion concentrations in said test solution.

* * * * *